(12) United States Patent
Bogie et al.

(10) Patent No.: US 9,320,907 B2
(45) Date of Patent: Apr. 26, 2016

(54) INTEGRATED SURFACE STIMULATION DEVICE FOR PAIN MANAGEMENT AND WOUND THERAPY

(71) Applicants: The United States Government, as represented by the Department of Veterans Affairs, Washington, DC (US); Case Western Reserve University, Cleveland, OH (US)

(72) Inventors: Kath M. Bogie, Shaker Heights, OH (US); Steven L. Garverick, Cleveland Heights, OH (US); Christian A. Zorman, Euclid, OH (US); Daniel S. Howe, San Diego, CA (US)

( * ) Notice: Subject to any disclaimer, the term of this patent is extended or adjusted under 35 U.S.C. 154(b) by 55 days.

(21) Appl. No.: 14/363,277

(22) PCT Filed: Jan. 18, 2013

(86) PCT No.: PCT/US2013/022139
§ 371 (c)(1),
(2) Date: Jun. 5, 2014

(87) PCT Pub. No.: WO2013/116013
PCT Pub. Date: Aug. 8, 2013

(65) Prior Publication Data
US 2014/0324120 A1 Oct. 30, 2014

Related U.S. Application Data

(60) Provisional application No. 61/594,105, filed on Feb. 2, 2012.

(51) Int. Cl.
*A61N 1/00* (2006.01)
*A61N 1/372* (2006.01)
*A61N 1/04* (2006.01)
*A61N 1/36* (2006.01)
*A61N 1/32* (2006.01)

(52) U.S. Cl.
CPC .......... *A61N 1/37217* (2013.01); *A61N 1/0468* (2013.01); *A61N 1/0492* (2013.01); *A61N 1/326* (2013.01); *A61N 1/36021* (2013.01); *A61N 1/37211* (2013.01)

(58) Field of Classification Search
CPC ........... A61N 1/36071; A61N 1/36021; A61N 1/36014
USPC ......................................................... 607/46
See application file for complete search history.

(56) References Cited

U.S. PATENT DOCUMENTS

2005/0187487 A1* 8/2005 Azizkhan ............. A61B 5/0215
600/561
2010/0042180 A1* 2/2010 Mueller ............... A61N 1/0456
607/46
2011/0270357 A1* 11/2011 Torgerson .......... A61N 1/36082
607/59

*Primary Examiner* — Amanda Patton
*Assistant Examiner* — Philip Edwards
(74) *Attorney, Agent, or Firm* — Gorman Law Offices; Robert Gorman

(57) ABSTRACT

The present invention provides a thin and flexible device and method of use thereof for pain and wound treatment of a subject. The integrated surface stimulation device may comprise a complete wireless stimulation system in a disposable and/or reusable flexible device for widespread use in multiple therapeutic applications. The invention would be situated on the skin surface of a patient and would be activated so as to reduce the overall occurrence of pain and/or increase wound healing rates. As provided, the device will comprise an integrated power supply and pre-programmable stimulator/control system mounted on the upper face of a flexible polymeric substrate layer. The lower face of the substrate layer will comprise areas of stimulating electrodes, applied using thin film coating techniques. The device can then be applied to the user with a medical grade pressure sensitive adhesive coating provided on the lower face of the substrate layer.

11 Claims, 5 Drawing Sheets

▨ LCP substrate

▧ Platinum

Fabrication sequence with a polyimide substrate

Si     polyimide     photoresist     Pt     Cr

FIG. 5

INTEGRATED SURFACE STIMULATION DEVICE FOR PAIN MANAGEMENT AND WOUND THERAPY

This application claims priority to U.S. provisional patent application No. 61/594,105, filed on Feb. 2, 2012, the contents of which are hereby incorporated by reference in the entirety.

FIELD OF THE INVENTION

The present invention relates to medical devices that utilize electrical stimulation for surface-stimulated treatment of pain and wounds in the human body. The present invention is a patch, i.e. a thin, partially flexible covering, which incorporates a stimulation controller, wireless communication device, miniaturized or wireless power, and a substrate with customizable treatment electrodes.

Open wounds can be difficult to treat. In particular, chronic wounds, such as ischemic wounds and pressure ulcers, are a major clinical challenge in the long-term care of people with physical impairment and/or disability. Even in mild cases, special care is required. Scientific studies show that electrical stimulation quickens wound healing, reduces scar formation, and can reduce discomfort therefrom. For example, galvanic treatment has been known for many years as a means to deliver drugs and cosmetic active agents into the skin for therapeutic purposes. Such approaches are based on mechanisms such as iontophoresis and electro-osmosis. A review of the literature reveals that galvanic treatment is also valuable in the treatment of wounds and scars, via several modes of action including accelerated cell regeneration; tissue repair; accelerated cutaneous barrier recovery (even with very low current); improved blood circulation; improved respiration; and scar reduction. Examples of such devices may be found in US Pat. Pub. No. 2010/0228180, titled "Power Source Electrode Treatment Device", PCT Pat. Pub. No. WO 2006/072834, titled "Stable Electrode and Uses Thereof, European Pat. Pub. No. EP 1448263, titled "Device for Controlled Delivery of Active Substance into the Skin, U.S. Pat. No. 7,922,676, titled "Disposable Electric Bandage", and US Pat. Pub. No. 2010/0030129, titled "Dermal Patch", each of which is hereby incorporated by reference in their entireties. In yet another example, clinical studies have used direct current (DC) electrical stimulation for electrotherapy. In summary, clinical studies have used different stimulation approaches and also surgical implantation, but to date no optimum electrotherapy protocol has been identified, especially for problematic wounds such as pressure ulcers.

Current approaches to electrical treatment have not been widely used in wound and/or pain therapy because these treatments comprise stationary, costly stimulation devices which are not convenient for home use. Furthermore, existing treatment protocols are simplistic administrations of electrical current that do not account for the need for varied modalities of treatments for specific wound types and pain associated therewith. More specifically, known approaches for wound treatment and ameliorating pain tend to require a high degree of technological expertise and training both for introduction and regular use, and often, surgical expertise is essential for implantation of these systems. Even where technologies are employed that negate the need for surgical implantation, existing devices are nevertheless intrusive and tend to disrupt other therapies and the activities of daily living in part because they utilize external wires and cables for use and powering of surface electrical stimulation devices. In addition to limiting patient mobility through the need to connect and disconnect wires whenever the patient moves, these very same wires are also a common source of device failure. Moreover, there has not been any notion either in literature or in common practice of combining wound care and pain treatment in wound therapy, or of providing customizable solutions to the exact treatment of the various forms of these maladies.

To this end, there is a recognized need for a simple, reliable, low-cost integrated surface stimulation device (ISSD) that can be used in a variety of mobile care settings, from the intensive care unit to the patient's home. It would be highly advantageous for this ISSD to have such an ISSD that employs electrical stimulation for wound and/or pain treatment, embodied on a thin and flexible substrate that includes a self-contained power source and controller. Preferably, such a system and device should be disposable and customizable for particular types of wounds and pain associated therewith, including the treatment protocol itself.

SUMMARY OF THE INVENTION

The present invention relates to a novel approach to improving the management of pain and wound healing through the use of an integrated surface stimulation device (ISSD). The ISSD for pain management, according to the present invention, is a wearable, flexible adhesive electrical stimulation patch that is wireless, with the totality of the component electronics and power source being wholly encapsulated thereon in a thin, flat instantiation. In providing the above, the invention utilizes advanced materials and fabrication techniques, and is designed so as to have a simple, user-friendly communication interface. More specifically, one embodiment of the invention contains all the components of a single-channel, current-controlled stimulation system within a lightweight, flexible, independently-powered portable device utilizing a custom, miniaturized (approximately 9 mm$^2$) Application-Specific Integrated Circuit (ASIC), also known as a custom IC. The ISSD uses advanced materials and cutting-edge fabrication techniques to provide sustained or intermittent application of Electrical Stimulation (ES) combined with maintenance of a stable wound healing environment. An optional software package with a graphical user interface (GUI) may also be provided for use on a partner device connected to the invented device, to be employed by a medical professional.

The ISSD comprises a complete wireless stimulation system in a disposable and/or reusable flexible device for widespread use in multiple therapeutic applications. The invented device would be situated on the skin surface of a patient and would be activated so as to reduce the overall occurrence of pain and/or increase wound healing rates. As manufactured, the device will comprise an integrated power supply and pre-programmable stimulator/control system mounted on the upper face of a flexible polymeric 'backbone' or substrate layer. The lower face of the substrate layer will comprise areas of stimulating electrodes, applied using thin film deposition techniques such as sputtering, evaporation, electroplating, and spray coating. The device can then be applied to the user with a medical grade pressure sensitive adhesive coating provided on the lower face of the substrate layer.

When provided as such, the invented system has features which also make it advantageous for patients when compared with conventional systems, in that it offers the advantage of electrical stimulation of the nerves that allows for better pain management, but does so in a miniaturized, wholly self contained reusable wireless adhesive patch-like device that can be worn on a patient's skin. To this end, the present invention overcomes the aforementioned and other disadvantages inherent in the prior art.

BRIEF DESCRIPTION OF THE DRAWINGS

With reference now to the drawings in detail, it is stressed that the particulars shown, are by way of example and for the purposes of illustrative discussion of embodiments of the present invention, and are presented for providing what is believed to be the most useful and readily understood description of the principles and conceptual aspects of the invention. In this regard, no attempt is made to show structural details in more detail than is necessary for a fundamental understanding of the invention, the description taken with the drawings making apparent to those skilled in the art how the several forms of the invention may be embodied in practice. Accordingly.

DETAILED DESCRIPTION OF THE PREFERRED EMBODIMENTS

Before explaining at least one embodiment of the invention in detail, it is to be understood that the invention is not limited in this application to the details of construction and the arrangement of the components set forth in the following description or illustrated in the drawings. The invention is applicable to other embodiments of being practiced or carried out in various ways. Also, it is to be understood that the phraseology and terminology employed herein is for the purpose of description and should not be regarded as limiting.

At its broadest level, the present invention relates to a medical device for treatment of wounds or pain comprising at least one electrically powered patch comprising ISSD circuitry that includes interconnecting wires on a substrate layer; at least one stimulation controller, the stimulation controller being configured so as to provide variable stimulation patterns; at least one configuration of electrodes attached to the substrate layer and in electrical connectivity with the at least one stimulation controller; at least one bi-directional wireless communication link, the bi-directional wireless communication link or module comprising at least one RF or infrared based interface; at least one power source electrically coupled to at least one configuration of electrodes and at least one stimulation controller. The ISSD must also include means for encapsulating the circuitry; and an adhesive means for attaching the substrate layer to a treatment surface. The device is fabricated from thin and flexible materials to enable at least those surfaces that contact a patient skin to conform to the contour of the patient, and may be processed with thick or thin film deposition techniques for application of the electrodes and other circuitry components, and may also provide for the power source to also feature a thin and flexible profile.

The principles and operation of powered treatment devices according to the present invention may be better understood with reference to the figures. The figures show exemplary embodiments of the present invention and are not limiting.

Figure 1:
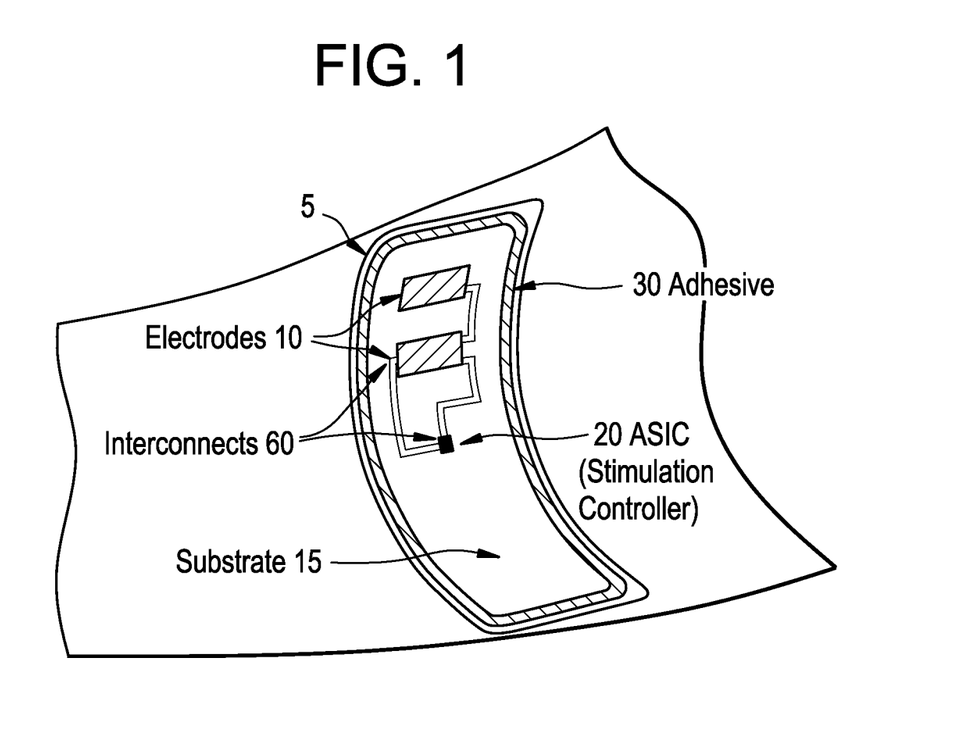
FIG. 1 is a photograph showing the physical appearance of an incomplete prototype of a wound treatment device as applied to a user, according to one embodiment of the invention.
Figure 2:
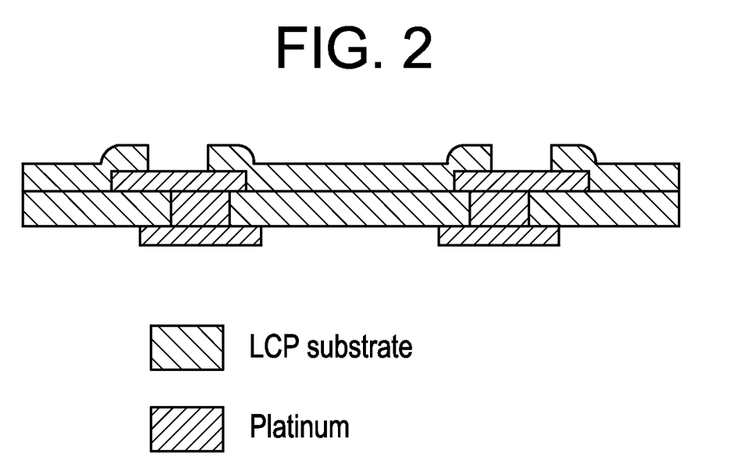
FIG. 2 is a schematic representation of an exemplary cross section of ISSD electrode-supporting substrate in accordance with one embodiment of the invention.
Figure 3:
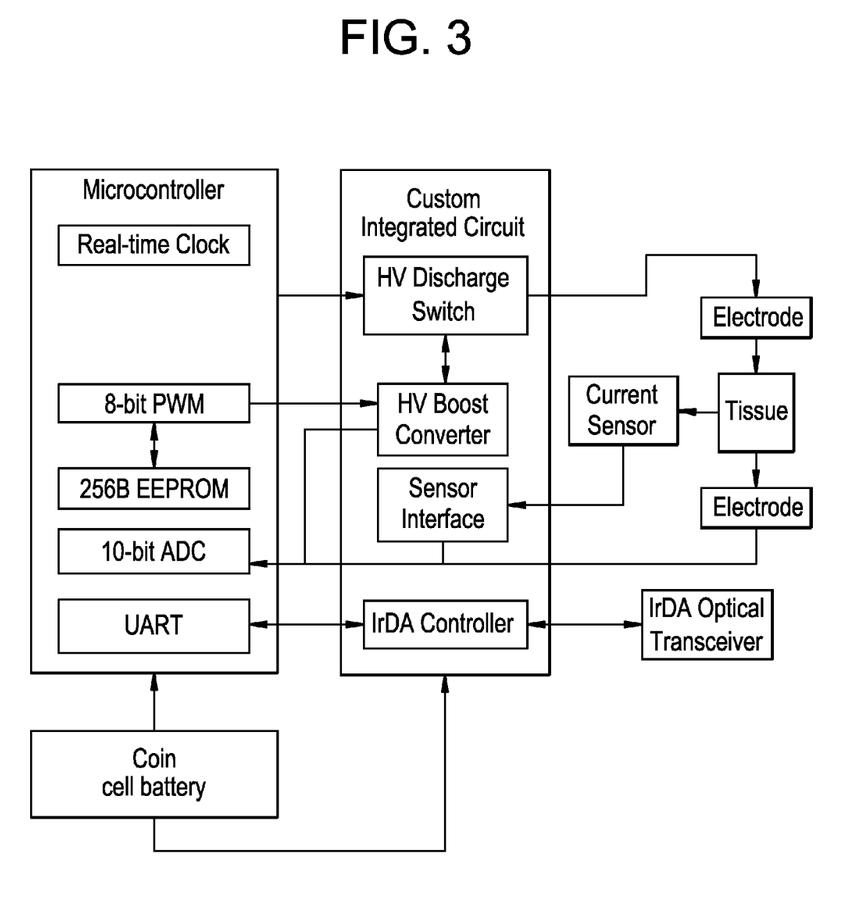
FIG. 3 is an illustrative block diagram of flexible ISSD circuitry 60 and related peripheral electronic components of the device according to one embodiment of the invention.
Figure 4:
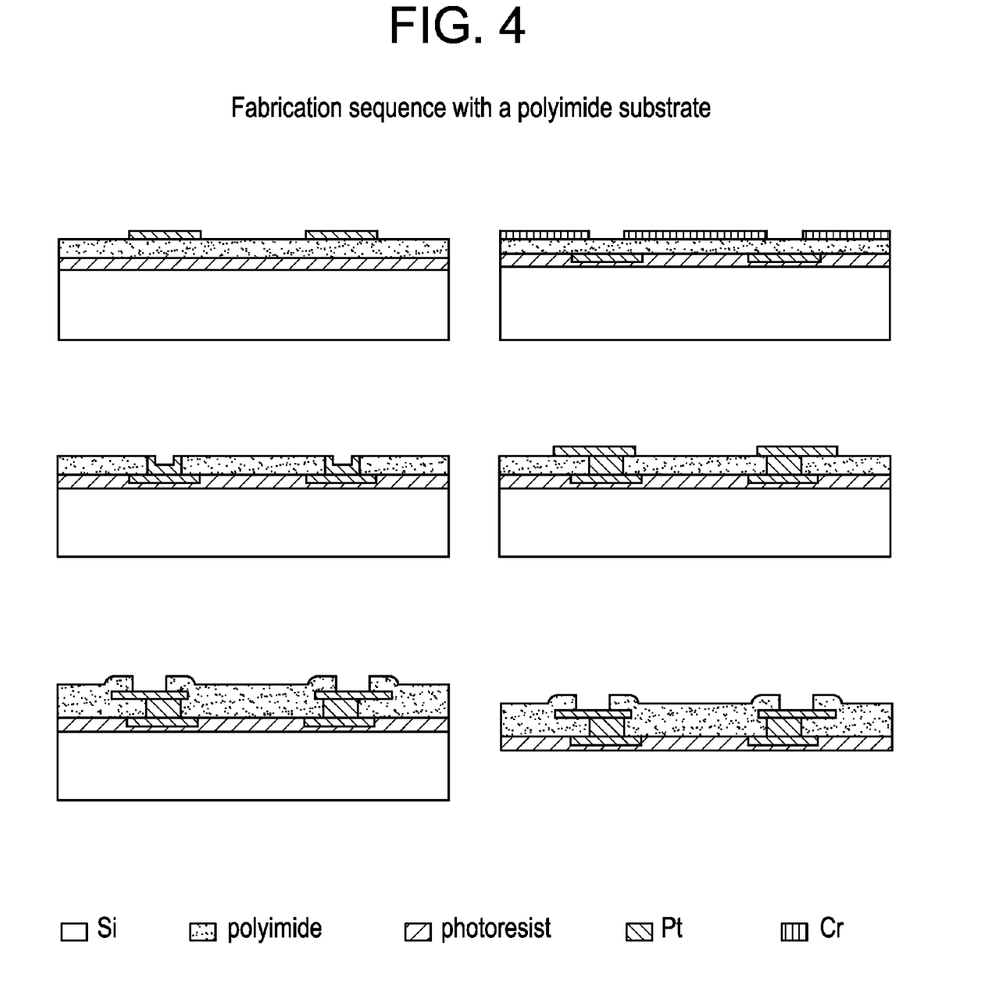
FIG. 4 is schematic cross-sectional views illustrating an exemplary fabrication sequence with polyimide substrate used in the device in accordance with one embodiment of the invention.
Figure 5:
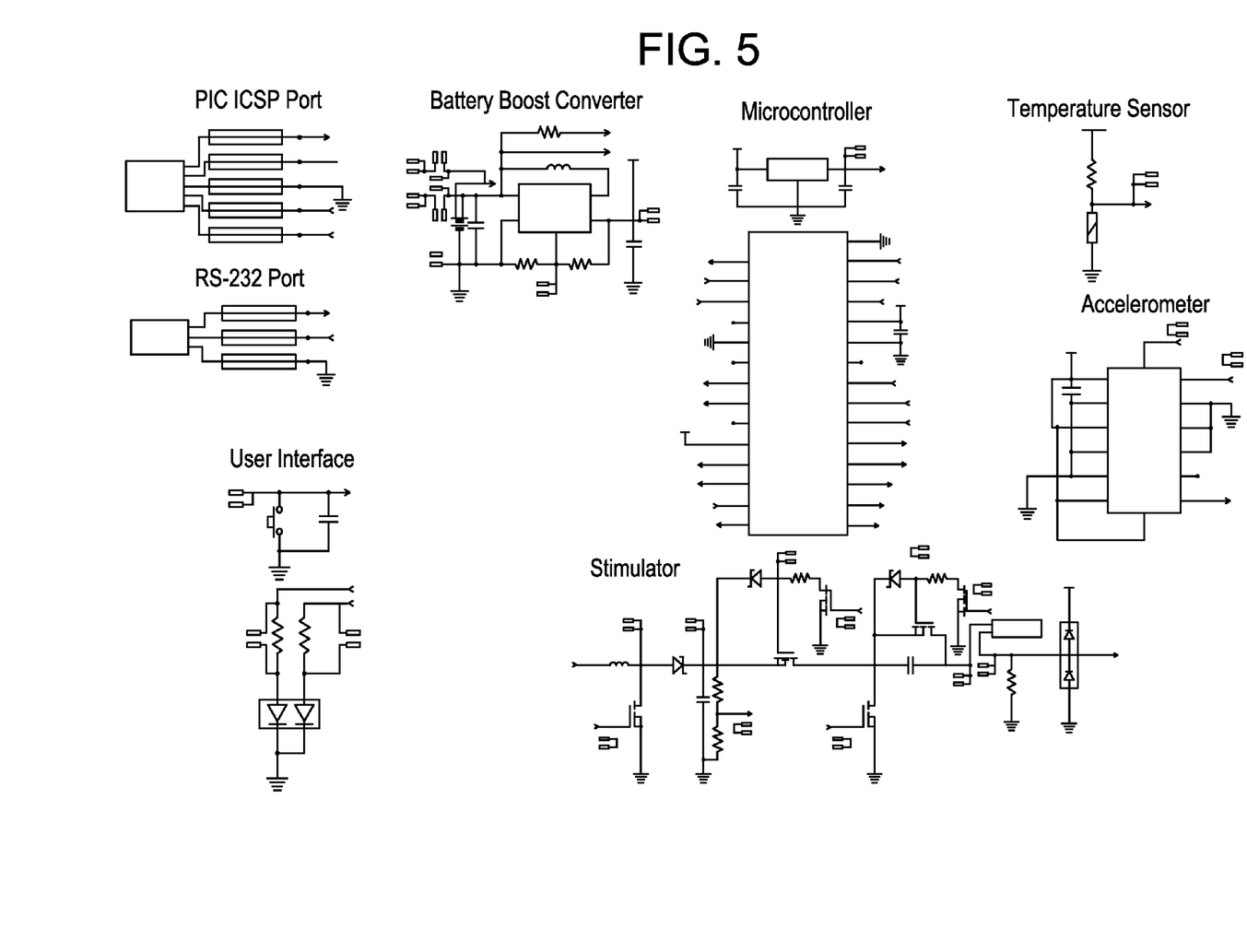
FIG. 5 is an electrical schematic diagram of one embodiment of the device according to the invention.

FIG. 1 shows one embodiment of a powered treatment device 5, including only the stimulation electrodes and controller components of the ISSD circuitry 60, where the latter has been fully implemented as an ASIC in order to reduce size and improve flexibility of the device. FIG. 2 shows the schematic cross-section of the supporting substrate, which is optionally made of flexible materials. FIGS. 3 and 5 show two additional embodiments of stimulation controller 20, one (FIG. 3) which employs an ASIC (custom IC) to implement only the high-voltage, sensing, and wireless communication modules 40 of stimulation controller 20, and another (FIG. 5) in which off-the-shelf (OTS) components have been used to implement these functions. In both embodiments, stimulation controller 20 must be interconnected with the electrodes 10 through interconnecting wires 17 (not specifically depicted) and electrically connected with power source or supply 50, all of which are carried by a disposable substrate layer 15. Power supply 50 and stimulation controller 20 components can be bonded to the upper face or side of substrate 15. Flexible stimulating electrode 10 regions can be microfabricated onto the lower face or side, which will be secondarily coated with a medical grade pressure sensitive adhesive for attachment to the user. Because one key design concept underlying inventive device 5 is forward compatible upgradeability, it is provided with a flexible or adaptable architecture that allows for the potential for functional expansion such as multi-channel stimulation and biofeedback sensor capability, which is provided as an alternate embodiment of the present invention. The device comprises an integrated power supply and pre-programmable stimulation controller 20 system mounted on the upper face of a flexible polymeric 'backbone' or substrate layer 15. The lower face of substrate layer 15 comprises areas of stimulating electrodes 10, applied using sputter coating techniques as described hereafter and as illustratively shown in FIG. 4. The device can be applied to the user with a medical grade pressure sensitive adhesive coating 30. In most cases, it may be helpful to have device 5 sterilized upon reuse or where not initially sterilized prior to placement over an open wound area of a patient. Many approaches may be used for this, and one illustrative sterilization could involve using an ethylene oxide, which is a low-temperature method that would allow device 5 to be fully sterilized, but would not damage the on-board electronics.

The controller circuitry or stimulation controller 20 provides functions such as timing, intermittent operation, and power monitoring, and combines with passive components, such as resistors, capacitors, an inductor and connective wiring (interconnecting wires 17, not specifically depicted), to produce stimulating waveforms. The duty factor of the high-voltage discharge pulses produced using stimulation controller 20 will be proportionally related to the average output power. The aforementioned passive elements are usually separate components, and may, in one embodiment, be mounted to a rigid circuit board (not depicted) and can be connected by printed wiring (also not depicted). However, a traditional rigid circuit board may not always meet design requirements (such as specific types of required flexibility) that may be required in some embodiments for stimulation controller 20. In either case, all electronic components herein must be minimized in quantity and size to maximize flexibility, as will be further discussed below.

Depending on the desired effect and system requirements, one may employ one of three possible illustrative embodiments, wherein the stimulation controller 20 comprises either: (i) two ICs (an IC microcontroller coupled with an ASIC stimulator); or (ii) a single IC (e.g., an IC microcontroller coupled with an OTS discrete stimulator); or (iii) a full-function IC, i.e. an ASIC that includes both stimulator and microcontroller functions, each of which is preferably miniaturized.

The ASIC embodiment may be either partially or completely based on an ASIC that may include all circuit functions required for actuation and sensing of the ISSD, as well as communication to the external computing device, such as a laptop computer, smart phone or the like, as contrasted with the discrete stimulator mentioned above which provides for these components separately. In either case, a high-voltage transistor may be required as part of a boost converter that provides the approximately 100-V level required for electrical stimulation in some circumstances. In one embodiment, all boost converter circuitry, excluding the aforementioned high-voltage inductor, diode, and storage capacitor components, could potentially be integrated onto the ASIC. Analog preamplifiers and analog-to-digital converter for sensing of electrode current and other biological signals of interest can also be fully integrated. Wireless communication circuits that comprise the wireless communications module 40 (discussed hereafter) can also be fully integrated, except for the infra-red (IR) photo diodes based embodiment required by the illustrative IrDA channel when used in a rigid circuit board-based embodiment. Because IR-based connectivity approaches require line-of-sight to a given partner device, in one illustrative embodiment, wireless communications can employ alternative wireless communication approaches such as the Bluetooth® Low Energy (version 4.0) standard, or other RF approaches for wireless communications module 40. The inventive flexible ISSD circuitry 60 may then comprise at least: (i) a stimulation controller 20 mounted on a circuit board which is in turn mounted on substrate layer 15, wherein the stimulation controller 20 has different embodiments, either two ICs (an IC microcontroller coupled with an ASIC stimulator); or a single IC (e.g., an IC microcontroller coupled with an OTS discrete stimulator); or a full-function ASIC that provides both microcontroller and stimulator functions, as discussed herein); (ii) a bi-directional wireless communications module 40 which includes connectivity to an IR interface (photodiode pair) or an RF interface required for wireless communication; (iii) a high-voltage boost converter circuit in electrical connectivity with stimulation controller 20, said high-voltage boost converter circuit comprising an appropriate high-voltage inductor/diode/storage capacitor as required by stimulation controller 20, said high-voltage boost converter circuit being charged to the aforementioned high-voltage level; (iv) power source 50 connected to the circuit board upon which stimulation board 20 is mounted; (v) stimulating electrodes 10 connected an interconnection means to the circuit board upon which stimulation board 20 is mounted; and (vi) the interconnecting means, wherein the interconnection means is provided for electrically connecting at least stimulating electrodes 10 with stimulation controller 20, the interconnection means illustratively including at least one or more components chosen from the group comprising: interconnecting wires 17 (not specifically depicted); thin film deposited structures; or thin film platinum interconnect structures in combination with a bonding, wherein the bonding is chosen from the group comprising wire bonding or flip chip bonding. In contrast to the full-function ASIC embodiment, the two-IC embodiment offers a separate high-voltage stimulator ASIC and microcontroller in order to permit straight-forward firmware upgrades and to minimize the cost of the ISSD, given that inexpensive OTS microcontrollers can be employed. This embodiment provides for the function of the stimulator to be preserved in the case where the microcontroller requires upgrading. The stimulator may be implemented using any preferred technology independent of the microcontroller and furthermore, may include sensory circuits such as for monitoring movement or other vital statistics in a user. In any case, the above ISSD circuitry can be encapsulated via an encapsulation means that protects the same from moisture and the like, all of which, when mounted on substrate layer 15, can be adhered to the skin of a user through the adhesive means described herein.

Regardless of the particular embodiment of stimulation controller 20, ISSD circuitry 60 may employ an aforementioned high-voltage boost converter circuit with a step-up loop that includes the aforementioned high-voltage transistor, and a storage capacitor that is rated for an illustrative maximum 100V, at an illustrative 100-nF capacity in order to maximize the voltage aspects of the overall system, and for increasing the (interchangeable) battery life of power source 50. In both the two-IC embodiment and the full-function ASIC embodiment, the step-up capacitor may be provisioned to be physically separate, off chip, but in electrical connectivity therewith. In the particular case of the two-IC embodiment, both ICs can be obtained in die form and can be 1) flip-chip bonded directly to metal traces on the flexible substrate, then sealed with protective coating, or 2) wire bonded to the lead frame of a standard surface-mount IC package that would then be hermetically sealed. The former is potentially smaller and more flexible, while the latter is simpler to manufacture and potentially more robust. Where an embodiment is desired that includes customized rather than OTS ICs, a custom IC (ASIC) could be fabricated using an illustrative 0.7-micron high-voltage CMOS foundry process provided by ON Semiconductor (available from ON Semiconductor of Phoenix, Ariz.), via the MOSIS service of Marina del Rey, Calif. Thereafter, it is noted that in the present invention, variable stimulation patterns are provided to accommodate different types of wounds and the changing treatment thereof over time. To this end, software can be pre-programmed on the microcontroller of a two-IC embodiment, or on the ASIC of a full-function ASIC embodiment. The various parameters that may be considered when providing such software within device 5 might, in one embodiment, be effected through usage of the below considerations set forth in Table 1, below.

TABLE 1

Specifications for conformable flexible modular surface stimulation (MSS) device

| Variable | Relevance | Criteria |
| --- | --- | --- |
| Safety | Prolonged contact with skin requires neither the materials employed nor the stimulation delivered will cause tissue damage | Substrate materials must be biocompatible & stimulation may be charge-balanced. |

TABLE 1-continued

Specifications for conformable flexible modular surface stimulation (MSS) device

| Variable | Relevance | Criteria | | |
|---|---|---|---|---|
| Reliability | In order to be effective, ES must be delivered as programmed. | Stimulation is ideally delivered consistently over an illustrative 7 day lifetime of the device. | | |
| Sterilization | Devices in contact with open wounds must be initially sterile to minimize infection. | May use illustrative ethylene oxide sterilization to achieve sterility while maintaining electrical functionality. | | |
| System configuration | | | | |
| Flexible | Chronic wounds occur on many parts of the body. | Conform to an arc equal in radius to a circumference of any rounded body parts. | | |
| Size | Device must be suitable for clinical use in a variety of wound locations. | Overall footprint will vary to fit target wound. | | |
| Electrode layout | Stimulating electrodes deliver therapeutic ES to the wound. | Electrodes to be located at the wound margins and can be patterned based on wound size and shape. | | |
| Low-profile & lightweight | Not interfere with overlying bedclothes or cause high pressure if accidentally lain on. | Maximum height less than 3 mm in one illustrative embodiment. Maximum weight less than 15 g in one illustrative embodiment. | | |
| System function | | | | |
| Wound occlusion | A moist microenvironment provides optimal wound healing | Maintenance of adherence to skin for up to 7 days with full wound occlusion. | | |
| User-friendly interface | Clinical acceptance requires ease-of-use. | Includes a customizable design for an intuitive GUI for selection and control of stimulation patterns. | | |
| Programmable | Optimal stimulation variables for ES therapy remain to be defined. Stimulation can be applied intermittently or continuous, for duty cycles from 5 min/day to 24 h/day. | Stimulation pulse variables may be based on data from prior clinical studies, illustratively described as: | | |
| | | | Range | Increment |
| | | Pulse width | 0-200 µs | 5 µs |
| | | Amplitude | 0-20 mA | 0.5 mA |
| | | Frequency | 0-20 Hz | 1 Hz |
| Power supply | Independent power supply, capable of 7 days use is required for un-tethered system. | Battery-powered, capable of up to 7 days continuous use. Battery will last longer with intermittent use. | | |

As mentioned above, the central core of present device 5 is comprised of a flexible polymeric biomaterial substrate (substrate layer 15) on which the flexible power supply 50 and rigid stimulation controller 20 will be attached along with the thin metallic electrodes and interconnects that are fabricated thereon. In certain illustrative embodiments, three different polymeric materials may be used to construct the flexible structures of the substrate layer 15, specifically materials such as polyimides, liquid crystal polymers, and thermoplastic polymers. In one particular embodiment, a combination of thick polyimide foils and thin film resins may be used for producing substrate layer 15 in order to meet the requirements for the device to be durable for longer periods in different environments, such as those encountered where use is needed for say, one week of continuous use in moist environments. One illustrative example of production of this variant of substrate layer 15 within the overall context of the present invention may be seen in FIG. 4, which details an exemplary process sequence for fabricating a flexible polyimide ISSD substrate. Substrate layer 15 may optionally be manufactured from any polymer material that is suitable for flexible electronics and biomedical uses according to a process that utilizes patterning that creates via structures thereon between the aforementioned circuit components through use of a micromachining step, or any suitable material which can accommodate the powered treatment device components.

Suitable materials include, but are not limited to woven material, non-woven material, polymers, or a combination thereof, and, in the case of woven materials might alternatively include the usage of smart fabrics which employ conductive traces on or within the fabric whether purely woven, knitted, sewn, couched, or whether provided as e-broidery and/or printed structures. Nevertheless, in one illustrative embodiment, substrate layer 15 may alternatively be made from liquid crystal polymers, polyimides, vinyl materials or polyester. Optionally, substrate layer 15 can be made up of a plurality of materials, which can be stacked or connected in a co-planar way by any suitable attachment means. In some embodiments, base layer substrate 15 is made up of one continuous piece of material. Substrate layer 15 may readily facilitate attachment of the overall device 5 to a desired body area. Attachment mechanisms may include but are not limited to medical grade adhesives, adhesive strips, suction cups and/or any combinations thereof. It has also been found that lower cost medical grade pressure sensitive adhesives such as Dermabond® (2-octyl cyanoacrylate, marketed under the aforementioned trademark by Johnson & Johnson of New Brunswick, N.J.) can be used, in one embodiment, to attach substrate layer 15 to intact skin. On removal, this type of medical grade pressure sensitive adhesive preferentially adheres to the substrate material, thus causing no skin damage, and can remain strongly adherent after many hours or days.

In one embodiment, the present invention provides flexible ISSD circuitry 60 to be situated on substrate layer 15 that is processed from an illustrative polyimide material that utilizes patterning processes in order to create via structures between the circuit components of flexible ISSD circuitry 60. One exemplary approach utilizes micromachining step, such as a KOH-based wet chemical etching step, in order to create the via structures depicted in FIGS. 2 and 4. Such an etchant is effective in removing polyimide, and the use of etchant-resistant materials such as platinum for electrodes 10 and the metallic etch mask can offer good resistance to the etchant. Alternatively, plasma etching, laser micromachining or other material removal techniques can be utilized to realize the same structures, but in either case, successful fabrication of the flexible ISSD circuitry 60 is critically dependent on the fabrication of effective interconnect structures that fill the microfabricated vias. Simultaneous electroplating on both the sidewalls and the bottom surface of the vias enables complete filling within an illustrative current thickness range of say, 10 microns. Alternative electroplating options may be afforded under ultrasonic conditions or with the use of 'filler' materials. Following fabrication of substrate layer 15 and interconnects thereon, the discrete components thereof can be mounted at designated locations on the (illustrative polyimide) substrate layer 15 using a conventional electronics packaging adhesive. Electrical connections that may comprise a part of an interconnection means or in one embodiment, interconnecting wires 17, between the discrete components and the thin film platinum interconnect structures may, in one illustrative embodiment, be made by wire bonding. Flip chip bonding can also be used to make secure electrical connections. The electrical connections can be mechanically secured, electrically isolated and environmentally protected by a third polyimide film of roughly the same thickness as the discrete components (0.5 mm) so as to ensure complete coverage of the wire bonds. It can be locally applied so as to not interfere with the global flexibility of the substrate. After localized polyimide encapsulation, the polyimide substrates can be removed from their silicon wafer pairs by a mild acetone soak or other appropriate methodology as known in the art.

In an additional embodiment, the present invention provides a method of production of device 5 and details of which, in terms of the illustrative materials and fabrication, are discussed henceforth. The central core of the device 5 is a flexible electrode-supporting substrate 15 comprised of a Liquid Crystalline Polymer circuit material (LCP) sheet with an 18 µm copper cladding layer on one of its surfaces, the fabrication sequences of which are illustratively described in one embodiment as seen in FIG. 4. In one embodiment, the electrode structures 10 are fabricated on the non-copper clad user-applied side of the LCP substrate 15 by photolithographic patterning, platinum thin film sputtering, and lift-off patterning. Electrodes 10 can be made of any suitable material, such as zinc, copper, manganese dioxide, iron, magnesium, silicon, sodium, silver, silver/silver chloride, carbon, graphite, platinum, nickel, gold, lithium or a combination thereof. Optionally, electrodes 10 can be made by any suitable technique. In some embodiments, electrode is made by a suitable printing technique. Electrodes 12 can be disposed in any suitable way on substrate 15 in spaced relation to power source 50 and electrically connected to power source 50 in any suitable way, or as described herein. Vias for vertical electrical interconnects between the two sides are then formed through the LCP by laser micromachining or plasma etching from the copper-clad component side to the back of the platinum electrodes. Platinum is sputter deposited on the sidewalls of the vias prior to electroplating to form a vertical interconnect between the bio side electrodes and the stimulation circuitry on the component side, as depicted in FIG. 2 and FIG. 4. Lateral interconnect structures are then fabricated by lithographic patterning and copper etching. The upper surface of the substrate 15 can be composed of a flexible barrier material (optionally part of the aforementioned encapsulation means) that provides a safe interface with the patient's environment, yet protects the electrical components from direct exposure to moisture, especially for the sensitive and delicate microprocessor chips and electrical interconnects. This packaging or encapsulation means must not impede the flexibility of the substrate, be impervious to impurity diffusion, be mechanically durable and be electrically insulating. Parylene is one embodiment for this application since it meets the design requirements and has been found to be a suitable candidate coating material for implanted medical devices. The lower side of substrate 15, which is intended to be applied to the skin of a patient, is secondarily coated with a medical grade pressure sensitive adhesive for attachment to the user, as part of the aforementioned adhesive means. The metalized surfaces on the component side are passivated by the application of a vapor deposited Parylene film and/or spin-castable polymer. Windows into the passivation layer can be formed by laser micromachining or plasma etching to facilitate electrical connection with discrete components, and can provide patterning in varying layouts as may be required for customized electrode patterns in specific applications involving particular (size/type) wound remediation and the like. In order to meet the need for customization, the above offers an aspect of provision for modularity wherein the electronic components of ISSD circuitry 60 can be mounted on a second LCP sheet that serves as the substrate for the reusable electronic components. Interconnect structures are fabricated on this LCP sheet using the methods described above. Therewith, further connections between the electronic components and the interconnect structures, including the interconnection means, can also be made by wire bonding or flip chip bonding. The reusable component substrate can then mounted on the electrode-supporting substrate using a conventional packaging adhesive. The reusable component substrate is mechanically secured, electrically isolated and environmentally protected by an encapsulating means of polymer film of roughly the same thickness as the discrete components (0.5 mm) so as to ensure complete coverage of wire bonds. The upper surface of substrate 15 of device 5 is thus composed of a flexible barrier material that provides a safe interface with the patient's environment in such a way that protects the electrical components but does not impede flexibility. Medical grade silicone can also be used to encapsulate the electronic components in order to further ensure biocompatibility, electrical compatibility as an encapsulating material for microelectronics, and for ease of overall application.

In terms of power supply, device 5 provides for varying approaches to power source 50, which typically requires provision of a requisite voltage that is necessary to generate stimulating waveforms. Power source 50 may comprise single-use batteries, however discharge characteristics must be repeatable to ensure reliable delivery of pre-programmed stimulation patterns. A flat power discharge profile that will provide consistent power for longer periods (e.g., approximately 7 days or so) of stimulation is desirable, although the inventive electronics design also allows for a somewhat sloped discharge profile. Therefore, any battery chemistry can be used. The battery must be thin, small, durable and strong. Power supply 50 can be modified in 1.5-V increments as necessary, but generally will be either 1.5 V or 3.0 V. To this end, power source 50 is ideally thin and flexible as specifically described below in one illustrative embodiment, but it can nevertheless be of any suitable size and shape that can accommodate the aforementioned requirements. In one embodiment, the power source 50 is depicted as a single electrochemical cell. However, power source 50 need not be limited to one cell, but may include a plurality of connected electrochemical cells, galvanic cells, batteries, with/without electronics configured to regulate the electrical potential (voltage) to the level required by the particular body area of the subject. In some embodiments, the current and or voltage supplied by the power source is fixed and cannot be adjusted by a user, although stimulation controller 20 can provide for any direct stimulation capability. The thickness of the illustrative electrochemical cell or power supply 50 may be in the range of about 4-20 mm thick. By way of example, a suitable electrochemical cell may be a button or watch battery, such as a lithium coin battery providing approximately 40 mA-hr at 3V, may be utilized. However, this may in some cases prove too heavy and bulky, and as such, in alternative embodiments, power supply 50 may be provided in a 1.5-V cell with step-up circuitry, with total battery current consumption for a nominal stimulation pattern of ~1 mA, thereby giving a battery life of say, 240 hours with a 15% stimulation duty cycle, or may also be provided as a thin cell applied using a suitable printing technique. Recent developments in battery technology have led to the development of very low profile, flexible 'ribbon' batteries, such as PowerPaper™ batteries (available from Graphic Solutions, Inc., Chicago, Ill.), which are ultra-thin (<1 mm thick) flexible batteries that can be directly printed onto a variety of surfaces. The cathode and anode layers of these illustrative batteries are fabricated from proprietary ink-like materials, thereby creating a 1.5-V battery that is thin and flexible and does not require bulky casing or encapsulation. In addition, the materials used in this illustrative battery, zinc and manganese dioxide, are classified by the Federal Drug Administration (FDA) as environmentally friendly, non-hazardous and may be disposed of without restriction. These types of batteries are capable of providing up to 1 mA continuous current. However, these ribbon type batteries often do not provide adequate power for longer periods, and may be useful for more temporary applications. Terminals for connection thereto may be located in any desired location to connect to the specific cell employed and may acquire any suitable shape and size, depending on the specific application.

Figure 6:
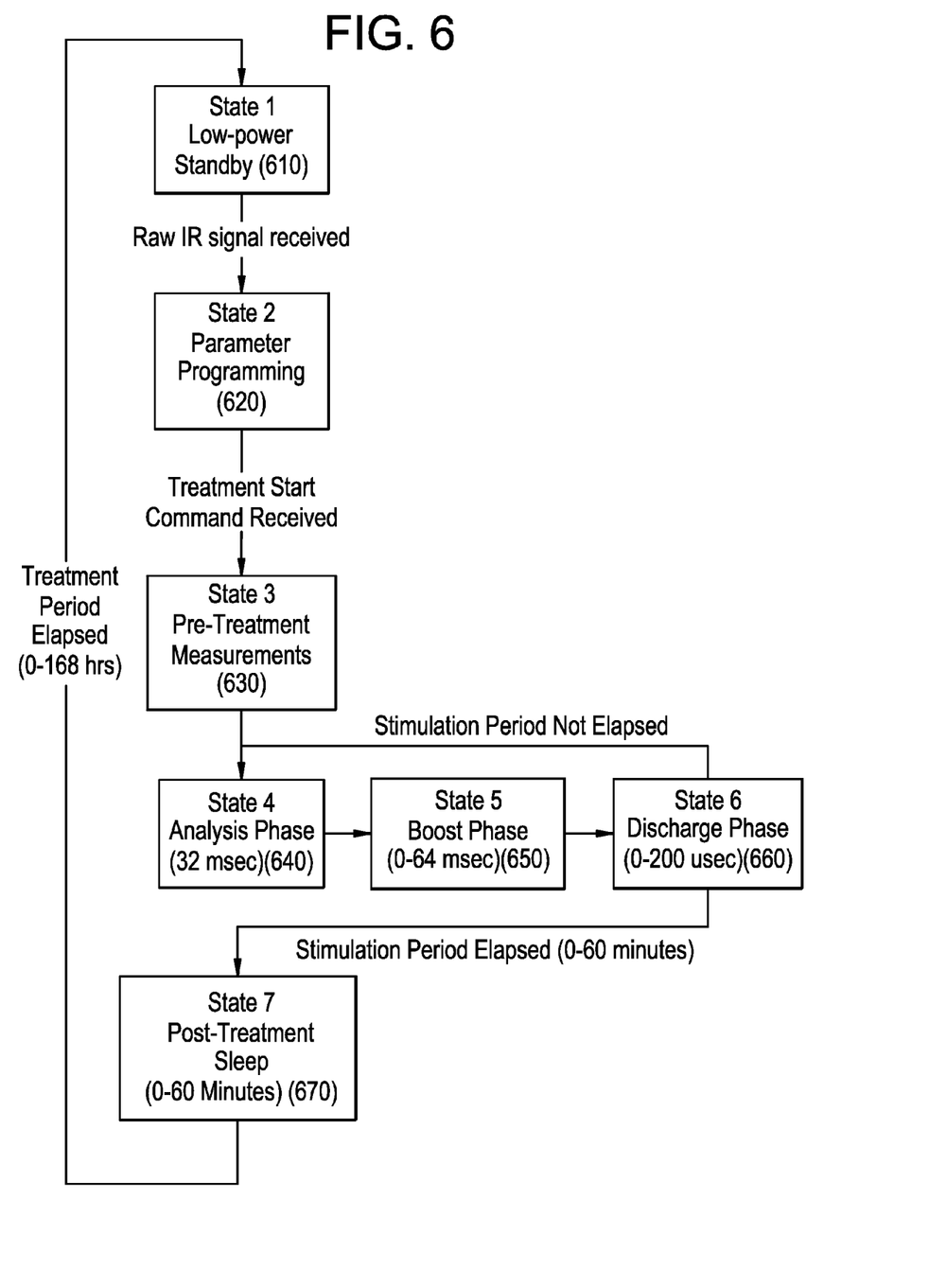
FIG. 6 is an operational flow diagram illustrating an exemplary treatment protocol utilized with one embodiment of the invention.

The invented device may be provisioned as a single-channel, single-pattern stimulator device, which would require a system control switch (not specifically depicted) to switch the operating state of device 5 between one of two states, off and on. However alternative embodiments of the device will also include the potential for multiple stimulation patterns and feedback to the clinician or technician through stimulation controller 20, which as discussed above, offers the capability for more sophisticated control, interrogation and feedback options. In providing such features, bi-directional wireless communication module 40 may further include an RF or an infrared communication link and protocol (such as an IrDA-based infrared communication link and protocol) that allows the ISSD to communicate via multiple channels with outside partner devices (not depicted) such as Personal Digital Assistants, computers, smart phones, tablets, lap tops, etc., so as to allow system control and retrieval of sensor data without a physical connection to device 5. In such an illustrative embodiment, the selected communication protocol might allow up to 256 units to be used in the same vicinity. If based on illustrative IrDA-type optical components, it is noted that the inherently narrow transmission focus thereof (approximately a 30 degree cone) can mitigate potential communications issues emanating from inventive device 5, because selection of a given partner device requires pointing the partner device at the inventive device 5 being programmed at any given time. Communication software can further be utilized for modifying stimulation parameters in stimulation controller 20 and for displaying stimulation waveform graphs on the partner device. To this end software to allow system control and retrieval of sensor data (e.g., outside control adjustment and feedback upload) using the link might be provided in accordance with the illustrative steps 610-670 as outlined in FIG. 6. Sensor data and other status parameters can be uploaded to the partner device and displayed to facilitate any necessary adjustments. Afterwards, any (bio) data provided from the sensors (electrodes 10) can be uploaded to the partner device for further analysis offline, if desired by a given medical professional. To this end, the aforementioned optional software package may also be provided with a graphical user interface (GUI) for use on a partner device connected to the inventive device, as employed by a medical professional.

When provided in accordance with the above, treatment device 5, including all device components, has an overall thin and flexible profile, which may suit the contour of a body area of a subject. Treatment device 5 may therefore be of any size, color and shape suitable for application to a desired body area. In some embodiments, the thickness of device 5 may limited to 10 mm to ensure flexibility, but may be thicker in other applications. The thickness of device 5 may also be dependent upon the type of material used and the flexibility of that material. In some embodiments device 5 may be partially and/or completely disposable. To this end, in some embodiments substrate layer 15 may be disposable, while the ISSD circuitry 60 may be reusable (modular, and therefore easily switched to a new replacement substrate layer 15), or alternatively, the whole device 5 may be deemed disposable. Regardless of which embodiment is chosen, device 5 must be stable over a wide range of temperatures and humidity levels, and may be used over all body areas of a patient or user, and to this end, may be designed or customized to fit any area of the body and to have any desirable size, according to the area to be treated. By way of further note, electrodes 10 can also be customized in terms of overall number, size, and distribution on substrate layer 15. The customization of electrodes is often less important when the application usage of device 5 is for pain treatments (which are better customized through the use of amplitude variations and the like for varied pain states). In the case of wound treatment, however, it is often important to be able to vary the aforementioned design parameters in order to adequately treat different types and sizes of wounds.

The device of the present invention can therefore be a fully integrated device or can be part of a kit with removable components so that the covering, battery source, etc. may be replaced as needed. The device may also be removed from the body area at the end of treatment time. Time of treatment can vary, and accordingly, the device in some embodiments can be removed from contact with the body area after a time period which can be predetermined, upon expiration of a timer, or which can be determined according to the desired treatment and/or until no more improvement can be seen. The treatment can optionally be a one-time treatment, or can be repeated in suitable time intervals any suitable number of times. Use of the present invention can facilitate temporary alleviation and elimination of the above conditions. Duration of effect can therefore be affected by time and frequency of application, stimulation pattern variables, type and amount of current used, and severity of condition. In one embodiment, the device is a dermal patch configured for home use. In other embodiments, the device can be applied in a supervised environment. To this point, treatment according to the present inventions may be beneficial in all body areas. Being thin, flexible and versatile in shape and form, the devices of the present invention can be designed to fit any area of the body and to have any desirable size, according to the area having the disorder.

One skilled in the art can appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. A device for treatment of wounds or pain comprising at east one electrically powered patch comprising:
   ISSD circuitry, comprising circuit components of:
      an interconnection means on a substrate layer;
      at least one sensor configured to sense wound healing;
      at least one stimulation controller attached to said substrate layer, said stimulation controller being configured so as to provide variable stimulation patterns in response to wound heating sensor data from said at least one sensor;
      at least one microfabricated configuration of electrodes attached to said substrate layer and in electrical connectivity, via said interconnection means, with said at least one stimulation controller;
      at least one bi-directional wireless communication module, said bi-directional wireless communication modules being chosen from the group consisting of at least one infrared based interface or at least one RF based interface;
      at least one power source electrically connected to said at least one configuration of electrodes and said at least one stimulation controller; and
   an encapsulation means for encapsulating said circuitry; and
   an adhesive means for attaching said substrate layer to a treatment surface.

2. The device of claim 1, wherein said ISSD circuitry includes a voltage boost converter circuit configured to maximize voltage aspects as well as battery life of said at least one power source in electrical connectivity with said at least one stimulation controller.

3. The device of claim 2, wherein said stimulation controller is mounted on a circuit board and is chosen from the group consisting of a one-IC embodiment or a two-IC embodiment.

4. The device of claim 3, wherein said one-IC embodiment is chosen from the group comprising: an IC microcontroller coupled with an OTS discrete stimulator; or a full-function ASIC microcontroller stimulator.

5. The device of claim 3, wherein said two-IC embodiment comprises an IC microcontroller coupled with an ASIC stimulator.

6. The device of claim 4 or 5 wherein said device is fabricated from thin and flexible materials to enable at least those surfaces that contact a patient skin to conform to the contour of the patient.

7. The device of claim 6, wherein the at least one power source is thin and flexible.

8. The device of claim 7, wherein said substrate layer is formed from the group comprising: polymer material suitable for flexible electronics and biomedical uses according to a process that utilizes patterning that creates via structures, as part of said interconnection means, between the circuit components through use of a micromachining step; or smart fabrics utilizing conductive traces.

9. The device of claim 8, wherein said polymer material is chosen from the group consisting of: liquid crystal polymer materials or polyimide materials.

10. The device of claim 9, wherein said electrical connectivity via said interconnection means between said configuration of electrodes and said at least one stimulation controller is provided through thin film platinum interconnect structures in combination with a bonding, said bonding being chosen from the group comprising wire bonding or flip chip bonding.

11. The device of claim 10, wherein the micromachining step is chosen from the group comprising: a KOH based wet chemical etching step; or a laser micromachining step.

* * * * *